United States Patent
Brunger et al.

(10) Patent No.: US 8,968,373 B2
(45) Date of Patent: Mar. 3, 2015

(54) CORTICAL TENTING SCREW

(75) Inventors: Jonathan M. Brunger, Memphis, TN (US); Jeffrey M. Badura, Memphis, TN (US); James B. Thomas, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1450 days.

(21) Appl. No.: 12/179,471

(22) Filed: Jul. 24, 2008

(65) Prior Publication Data

US 2010/0023064 A1 Jan. 28, 2010

(51) Int. Cl.
| | |
|---|---|
| *A61B 17/04* | (2006.01) |
| *A61B 17/56* | (2006.01) |
| *A61B 17/58* | (2006.01) |
| *A61B 17/86* | (2006.01) |
| *A61F 2/08* | (2006.01) |
| *A61F 2/30* | (2006.01) |
| *A61C 8/02* | (2006.01) |
| *A61B 17/00* | (2006.01) |
| *A61C 8/00* | (2006.01) |

(52) U.S. Cl.
CPC ........... *A61B 17/8605* (2013.01); *A61C 8/0006* (2013.01); *A61B 17/863* (2013.01); *A61B 17/866* (2013.01); *A61B 2017/00893* (2013.01); *A61B 2017/8655* (2013.01); *A61C 8/001* (2013.01)
USPC ............................................. 606/308; 606/64

(58) Field of Classification Search
CPC ..................... A61B 17/86–17/869; A61C 8/00
USPC ............................. 606/64, 66, 86 R, 305, 308
See application file for complete search history.

(56) References Cited

U.S. PATENT DOCUMENTS

| | | | |
|---|---|---|---|
| 3,579,831 A | 5/1971 | Stevens et al. | |
| 5,176,680 A | 1/1993 | Vignaud et al. | |
| 5,201,733 A | 4/1993 | Etheredge, III | |
| 5,755,575 A | 5/1998 | Biggs | |
| 5,779,706 A * | 7/1998 | Tschakaloff | .................. 606/281 |
| 5,839,899 A | 11/1998 | Robinson | |
| 5,899,940 A | 5/1999 | Carchidi | |
| 5,971,985 A | 10/1999 | Carchidi et al. | |
| 5,972,368 A | 10/1999 | McKay | |
| 6,120,292 A | 9/2000 | Buser et al. | |

(Continued)

FOREIGN PATENT DOCUMENTS

| | | |
|---|---|---|
| DE | 43 29 788 | 5/2007 |
| EP | 1 688 103 A1 | 8/2006 |

OTHER PUBLICATIONS

Ace Bone Grafting and Ridge Split Augmentation Catalog, 2004; see p. 4.

(Continued)

*Primary Examiner* — Sameh Boles
(74) *Attorney, Agent, or Firm* — Sorell Lenna & Schmidt LLP (57) ABSTRACT

An implantable screw system for maintaining horizontal and/or vertical space during bone grafting procedures is provided, the screw comprising: a contoured head having a region adapted to support soft tissue and permit bone growth; a threaded shaft and a tip adapted to penetrate bone tissue; and where one screw contains a threaded chamber for engaging a second screw for additional space maintenance; wherein the screw(s) comprises cortical bone material. Methods of implanting one or more screws during bone grating procedures are disclosed.

20 Claims, 2 Drawing Sheets

(56) References Cited

U.S. PATENT DOCUMENTS

| | | | |
|---|---|---|---|
| 6,146,420 A | 11/2000 | McKay | |
| 6,238,214 B1 | 5/2001 | Robinson | |
| 6,283,973 B1 * | 9/2001 | Hubbard et al. | 606/104 |
| 6,290,500 B1 | 9/2001 | Morgan et al. | |
| 6,394,807 B2 | 5/2002 | Robinson | |
| 6,632,245 B2 * | 10/2003 | Kim | 623/13.14 |
| 6,761,738 B1 | 7/2004 | Boyd | |
| 6,949,100 B1 | 9/2005 | Venturini | |
| 7,090,493 B2 | 8/2006 | Chang | |
| 7,166,570 B2 | 1/2007 | Hunter et al. | |
| 7,309,232 B2 | 12/2007 | Rutherford et al. | |
| 7,322,978 B2 | 1/2008 | West, Jr. | |
| 2003/0105465 A1 * | 6/2003 | Schmieding et al. | 606/73 |
| 2004/0254578 A1 * | 12/2004 | Vaughan | 606/61 |

OTHER PUBLICATIONS

Kao, et al.; Tissue Engineering for Periodontal Regeneration; CDA Journal, vol. 33, No. 3, pp. 205—Mar. 2005.

Rose; Bone Grafts and Growth and Differentiation Factors for Regenerative Therapy: A Review; Prac. Proc. Aesthet. Dent. 2001; 13(9):725-734.

* cited by examiner

CORTICAL TENTING SCREW

BACKGROUND

The successful use of dental implants has long been known and is well documented in the field. Despite successful dental implant procedures through the years, the success of the placement of a dental implant is limited by the quality and quantity of existing bone of a given patient. Due to the destructive nature of dentures to the underlying jawbone the amount of bone in many people is very limited for the placement of dental implants.

Furthermore, atrophy of the jawbone can occur when the bone is not subjected to occlusal loads. Therefore, atrophy may occur over time when a tooth is not replaced with a dental implant. As a result, when a person has been partially edentulous for a long period of time, they may suffer from an atrophic alveolar ridge that is not capable of securely supporting a dental implant. The deterioration of the alveolar ridge has severe consequences, including reducing one's ability to masticate and compromising aesthetics.

In this situation, bone grafting has become an essential element for the successful treatment of those who do not have enough bone for dental implants. There are many known methods of bone grafting. As viable methods, blocks of hip bone have been affixed to the jaw and freeze-dried demineralized bone protein has been used as a stimulant to cause the patient's bone cells to become active and lay down new bone onto the existing bone areas and into the new bone graft areas. Through experience and research, it has become evident that, for bone grafting to be successful, it must be given an isolated space to grow, protected from muscular pressure, tissue impingement and forces of mastication. In order to create this space, fabric-like membranes or barriers have been used over a bony defect. Although this barrier creates an isolated space from the invasion of epithelial cells into the bony defect or bone graft area, it does not create a protected space from chewing forces or tissue pressure. It is necessary to protect the growing bone from all aspects of potential harm. Titanium meshes can be used to achieve this space maintenance; however, this technique has draw-backs, as the titanium mesh must be removed in subsequent surgical procedures.

In many instances the space is created and maintained utilizing dental implants and supports including a tenting-type support screw. Often, the head of the tenting-type support screw is placed away from the bone, providing enough space for placement of bone graft material and subsequent bone growth.

Implantable screws such as the tenting-type screw in this case have commonly been made of surgical quality metals, such as stainless steel, and surgical grade titanium and titanium alloys. Other commonly used materials include ceramics and various plastics. However, the use of these materials have many drawbacks. For example, metal screws typically remain in the body unless they are later removed by a separate operation. Further, metal screws can potentially irritate tissue in close proximity to the screw, shed harmful ions into the body, or loosen to the point of injury among other things. Other commonly used materials offer a comparable list of drawbacks.

SUMMARY

In some embodiments, new implantable devices comprising cortical screw material are provided for maintaining proper spacing during bone grafting in certain dental regenerative procedures. In some embodiments, the screw comprises cortical bone material and can become incorporated into the newly generated alveolar ridge, reducing or eliminating the need to have the screw removed prior to the placement of dental abutment/prosthesis. In some embodiments, the contoured-shaped head of the screw ensures an interface between the gingiva and the screw, minimizing the likelihood of dehiscence and creating greater space for the bone growth. In some embodiments, a multi-screw system is provided that allows one screw to engage another, providing space maintenance in multiple spatial vectors. The combination of more than one screw reduces the need for a staged bone grafting procedure where vertical and horizontal augmentations are performed separately.

In various embodiments, an implantable device for maintaining space during bone grafting procedures is provided comprising at least one screw, the screw comprising a contoured head, a threaded shaft and a tip adapted to penetrate bone tissue, wherein the screw comprises cortical bone material.

In various embodiments, an implantable device is provided for maintaining space during bone grafting procedures comprising a first screw wherein the first screw comprises a contoured head, a threaded shaft and a tip adapted to penetrate bone tissue. In various embodiments, the first screw further comprises a chamber disposed below the contoured head above the tip. In addition to the first screw, some embodiments provide a second screw comprising a head, a shaft and a tip, wherein at least the tip and a portion of the shaft of the second screw are adapted to be received by the chamber of the first screw. In some embodiments, the chamber of the first screw is adapted to receive at least the tip and a portion of the shaft of the second screw.

In various embodiments, an implantable device is provided that can be used in conjunction with a method of grafting bone in oral procedures. The method comprising, implanting into the jawbone an implantable device wherein an implantable device comprises a first screw comprising a contoured head, a threaded shaft and a tip adapted to penetrate bone tissue. In some embodiments, the first screw further comprises a chamber disposed below the contoured head and above the tip. In addition to the first screw, some embodiments of the present teachings provide a second screw comprising a head, a shaft and a tip, wherein at least the tip and a portion of the shaft of the second screw are adapted to be received by the chamber of the first screw. In various embodiments, the chamber of the first screw is adapted to receive at least the tip and a portion of the shaft of the second screw. The method comprises inserting the second screw into the chamber of the first screw.

Additional features and advantages of various embodiments will be set forth in part in the description that follows, and in part will be apparent from the description or figures, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "an implantable device" includes one, two, three or more implantable devices.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

In some embodiments, an implantable screw is provided for maintaining space during bone grafting procedures in a patient in need of such treatment, the screw comprising: a contoured head having a region adapted to support soft tissue; and a threaded shaft and a tip adapted to penetrate bone tissue; wherein the screw comprises cortical bone material.

The screw can be used to treat orofacial diseases, such as for example by way of illustration and not limitation, oral and maxillofacial surgical procedures for alveolar ridge preservation and/or augmentation as well as other surgical procedures. The term "orofacial disease" is intended to encompass diseases within the orofacial environment, as well as diseases that originate in the orofacial environment.

Treating or treatment of a disease refers to executing a protocol, which may include implanting one or more implantable screws to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

In some embodiments, the tenting screw system disclosed herein allow surgeons to utilize existing bone graft materials to treat bony defects in which space maintenance is crucial for success, but in which limited options for maintaining that space currently exist. Various embodiments of the present application permit oral surgeons to use an implantable screw system that need not be removed surgically, as the implantable screw(s) comprises cortical bone that will incorporate into regenerated bone. Further, the implantable screw is designed to have an interface that will not be harmful to the overlying gingival or mucosal tissue. In various embodiments, the implantable screw provides an attractive option to surgeons seeking space maintenance materials to use with bone grafting and bone regenerative products.

In various embodiments, the tenting screw system provides space between the bone and gingiva and supports the gingiva, allowing for placement of bone graft and bone growth adequate for restoration of proper jaw structure for proper aesthetics and for dental implant-borne restorations.

In various embodiments, the tenting screw system comprises bioresorbable material. By "bioabsorbable" or "bioresorbable" it is meant that the screw will eventually be broken down and be absorbed or resorbed within the human body, for example, by a bone cell and/or bone tissue.

Cortical Bone

In various embodiments, the screw of the present application comprises cortical bone material. Cortical bone, or compact bone, is one of two main types of osseous tissue. Cortical bone is dense and forms the surface of bones, contributing 80% of the weight of a skeleton. It is extremely hard and comprises multiple stacked layers with few gaps. The cortical bone can be obtained from human autologous bone and/or allograft tissue. Autologous and/or allograft tissues are not only biocompatible, but they are strong, and biointegrate in time with the recipient patient's tissue and can be shaped in to a screw commercially in a manufacturing environment. The cortical bone can be provided in a sterile form.

Typically, microstructure of cortical bone contains bundles, or fibers, of mineralized collagen that are oriented parallel to the long axis of the bone. Known methods for making demineralized bone particles involve subdividing sections of whole, i.e., mineralized, bone, e.g., by such mechanical operations as shredding, milling, shaving, machining, etc., to provide particles which are then demineralized, e.g., by treatment with acid. The resulting demineralized bone particles exhibit osteoinductive and osteoconductive properties that make them useful as, or in, implants intended for use in oral procedures such as bone enhancement in oral mandible and maxilla procedures, such as for example, alveolar ridge augmentation. In some embodiments, the screw would provide minimal surface demineralization so that the structural capacity of the screw is not compromised.

It will be understood by those of ordinary skill in the art that the cortical bone material may be obtained from non-human sources (e.g., bovine, ovine, porcine, or the like), such as for example, xenograft material from animal-derived bone tissue.

In various embodiments, the screw comprises as a component all or substantially all cortical bone material. "Substantially" or "substantial" includes largely but not entirely. For example, substantially can mean about 50% to about 99.999%, about 55% to about 99.999% or about 70% to about 99.999%, or about 80% to about 99.999%. or about 90 to about 99.999%.

In various embodiments, the cortical bone may be microtexturized to allow for increased bone apposition compared to machined surfaces.

Therapeutic Agents

The implantable screw system can be mixed, sprayed and/or coated with one or more therapeutic agents to provide an effective amount of the therapeutic agent. Therapeutic agents include, but are not limited to, analgesics, anti-inflammatory agents, anti-infective agents, antibiotics, bisphosphonates or other anti-resorptive agents (e.g. calcitonin), and/or growth factors. Bisphosphonates include, but are not limited to, pamidronate, alendronate, zolendronate, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3(methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bishosphonic acid; 1-hydroxy-3-(pyrrolidin-1-yl)propane-1,1-bisphosphonic acid, 1-(N-phenylaminothiocarbonyl) methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); or 1-hydroxy-2-(imidazo[1,2-a]pyridin-3-yl)ethane-1,1-diphosphonic acid, e.g. YM 529, or combinations thereof or the like.

An effective amount of the therapeutic agent is such that when administered, the drug results in alteration of the biological activity, such as, for example, inhibition of inflammation, reduction or alleviation of pain, etc.

"Analgesic" refers to an agent or compound that can reduce, relieve or eliminate pain. Examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

In various embodiments, the therapeutic agent can comprise BMPs and/or CDMPs including, but not limited to, BMP-2, BMP-4, BMP-6, BMP-7, BMP-8, and CDMP-1.

Anti-infective agents to treat infection include by way of example and not limitation, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; cefloranide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodiumr; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium;

talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In various embodiments, the screw comprises non-cortical bone material, such as for example, polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon fiber, glass fiber, plastics, ceramics or combinations thereof.

In various embodiments, the screw comprises biopolymers including but not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ,-caprolactone, dextrans, vinylpyrrolidone, polyvinyl alcohol (PVA), PVA-g-PLGA, PEGT-PBT copolymer (polyactive), methacrylates, poly (N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

The screw can be used for alveolar ridge augmentation, where increase in volume and bone is desired. An alveolar ridge (also known as the alveolar process) comprises the portion of bone in the upper jaw (the maxilla) or the lower jaw (the mandible) that surrounds and supports the teeth. Often, these areas do not contain enough native bone for dental implant placement or stabilization, and thus, the volume of bone needs to be increased. In various embodiments, the tenting screw provides space between the bone and gingival and supports the gingival so that bone can regenerate and restore the proper jaw structure for proper aesthetics and for dental implant-borne restoration.

The figures and corresponding descriptions below are not meant to limit the disclosure in any way; embodiments illustrated and described in connection with any one figure may be used in conjunction with embodiments illustrated and described in connection with any other figure unless otherwise expressly provided.

FIGS. 1-7 illustrate various embodiments of tenting screws for use as implantable devices generally referred to by the reference numerals 100-710, respectively. Similar reference numbers will be used throughout the drawings to refer to similar portions of similar parts.

Figure 1:
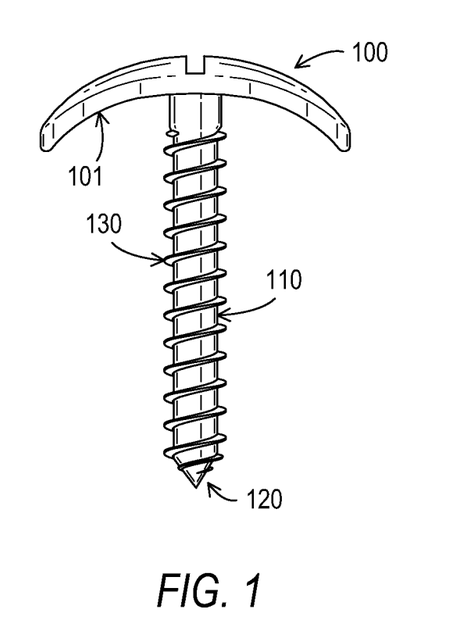
FIG. 1: illustrates an embodiment of an implantable device including a contoured head, a threaded shaft and a tip adapted to penetrate bone tissue.

FIG. 1 illustrates various embodiments of an implantable device provided for maintaining or creating space during bone grafting in certain dental regenerative procedures. In various embodiments an implantable device is a screw comprising a head 100, a shaft 110, and a tip 120 adapted to penetrate bone tissue. In various embodiments, the screw substantially comprises cortical bone material. In many embodiments, a screw comprising cortical bone can be integrated into the new bone as it grows. The integration of the cortical screw into the newly forming bone tissue reduces the need to remove the screw as is normally the case with screws of other compositions.

In various embodiments, the head 100 of the screw is contoured. For example, the screw head may be concave. The rounded shape of the head 100 ensures that the interface between the gingival and the screw head 100 minimizes the likelihood of dehiscence or piercing of the soft tissue in the jaw region.

In various embodiments, the first or second screw head comprises an under surface 101 that is curved or substantially curved. By providing a curved or substantially curved under surface of the screw, more space is provided between the gingival tissue and bone and thus the bone volume can be increased.

Gingival tissue includes part of the soft tissue lining of the mouth. It surrounds the teeth and provides a seal around them. Compared with the soft tissue linings of the lips and cheeks, most of the gingiva are tightly bound to the underlying bone and are designed to resist the friction of food passing over them.

In various embodiments the head 100 of the screw could range in size from about 3 mm to about 10 mm in diameter. In various embodiments, the head can be about 3 mm, 4 mm, 5 mm, 6 mm, 7 mm, 8 mm, 9 mm, or about 10 mm in diameter.

In many embodiments, the screw head 100 and undersurface 101 provide that sufficient space is maintained or created for grafting areas of the alveolar ridge, allowing the graft to either induce new bone formation or serve as an osteoconductive scaffold as bone forms in the space provided. 0-20 mm of space should be maintained between the native bone and the tented soft tissue. While bone is forming, the cortical screw remodels or integrates into the newly generating one, thus obviating the need to ever remove these screws.

In various embodiments, the shaft of the screw is threaded 130 from the head 100 to the tip 120. The threading 130 of the screw allows the screw to be anchored in the jaw by the user (e.g., surgeon, dentist or other health care provider). In various exemplary embodiments the pitch of the threading allows for primary stability after engagement of about 1 mm to 5 mm, or from about 3 mm to about 4 mm of bone. In some embodiments, the screw can be positioned for use in a variety of procedures including those procedures requiring only vertical or only lateral augmentation of the alveolar ridge.

In some embodiments, an implantable device for maintaining space during bone grafting procedures comprises a combination of multiple screws. In various exemplary embodiments, an implantable device comprises at least two screws that are capable of engaging each other, such that one screw is inserted into another screw.

Figure 2:
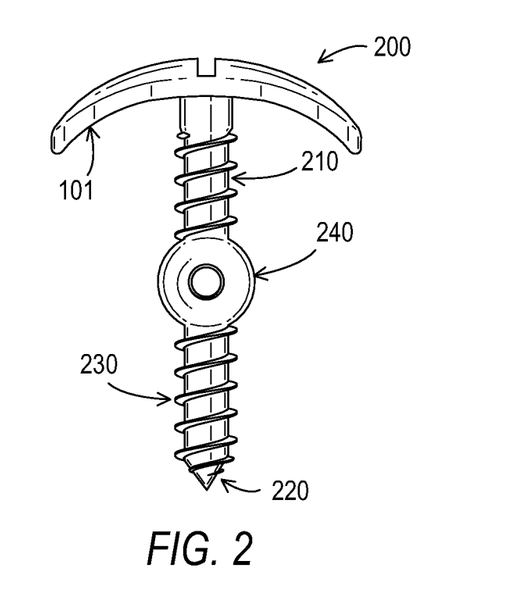
FIG. 2: illustrates an embodiment of an implantable device including a contoured head, a partially threaded shaft, a tip adapted to penetrate bone tissue, and a chamber disposed on the shaft to engage a second screw.

FIG. 2 illustrates various embodiments of an implantable device for maintaining space during bone grafting procedures wherein an implantable device comprises a screw comprising a head 200, a shaft 210, and a tip 220 adapted to penetrate bone tissue. Similarly to the screw described in an embodiment of FIG. 1, the screw comprises substantially cortical bone material to promote integration into the new bone. In some embodiments, the head 200 of the screw can be contoured and/or rounded to support the bone growth and ensure that the interface between the gingival and the screw head minimizes the likelihood of dehiscence or piercing of the soft tissue in the jaw region.

In some exemplary embodiments, the shaft 210 of the screw is only partially threaded 230. In some embodiments the threading 230 of the screw initiates at the tip 220 of the screw and proceeds up the shaft 210 providing at least enough threading 230 to ensure stabilization of the screw. In various embodiments, the thread pitch is sufficient to stabilize the screw after engaging about 3mm to about 4mm of bone.

Figures 6, 7:
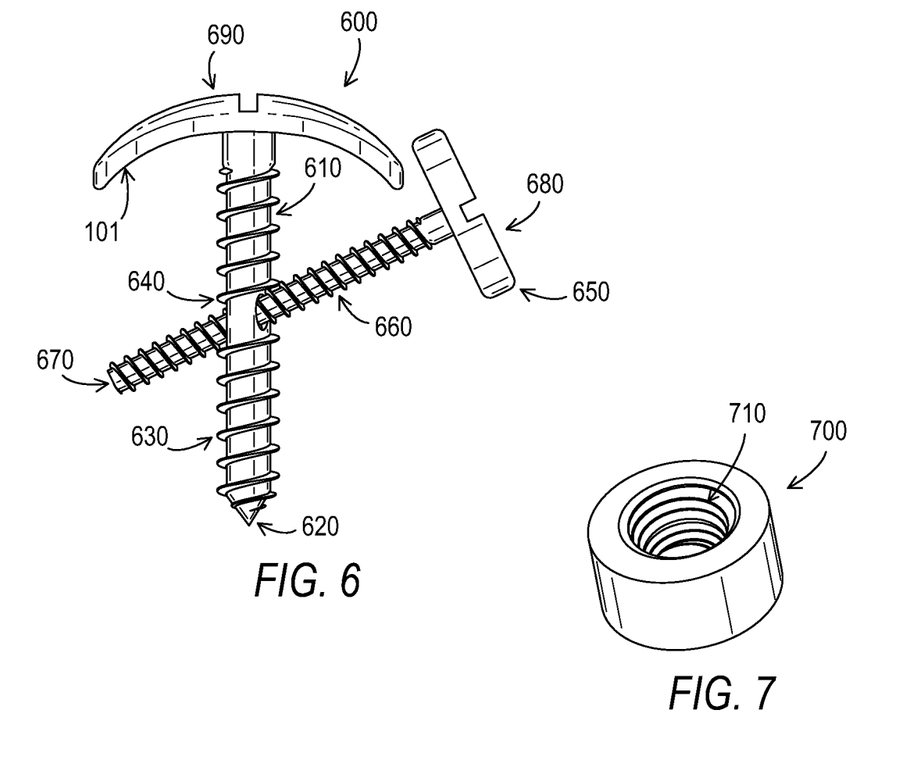
FIG. 6: illustrates an embodiment of an implantable device including a second screw engaged in the chamber of the first screw at an angle that is not perpendicular to the first screw.
FIG. 7: illustrates an embodiment of an element of an implantable device including a threaded chamber for location on the shaft of the first screw in order to receive a second screw.

In some embodiments, between the end of the threading 230 and the contoured head 200, the shaft 210 of the screw comprises a chamber 700 traversing the body of the shaft 210. FIG. 7 illustrates an exemplary embodiment of the chamber of the implantable screw. Chamber 700 has threading 710 such that the chamber 700 is capable of engaging mating threading of a second screw. In some embodiments, the second screw includes threading of the same pitch as the threading in the chamber, such that the second screw can be securely engaged in the chamber of the first screw by engaging the tip and threading of the first screw with the tip and mating threading of the second screw. The screw heads of the first and second screw can be turned by hand, drill or other dental instrument designed to turn the screw clockwise or counterclockwise as needed so that the tip can penetrate the bone.

In some embodiments, the chamber threading 710 and the threading of the shaft of the second screw can be the same as the thread pitch of the shaft of the first screw or a different threading pitch than the shaft of the screw including the chamber.

Figure 3:
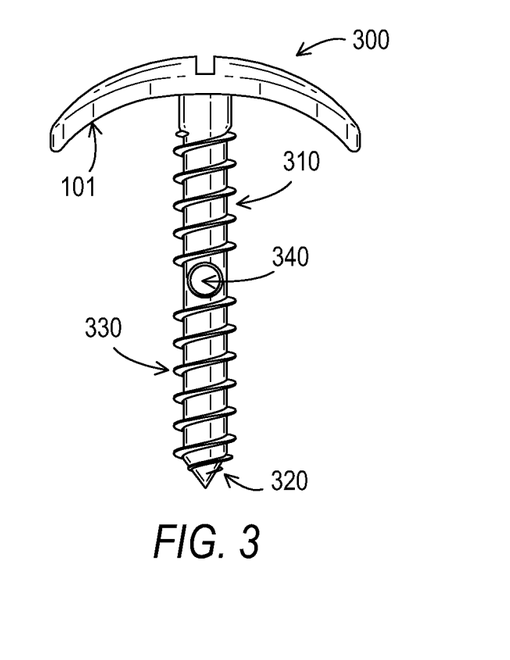
FIG. 3: illustrates an embodiment of an implantable device including a contoured head, a completely threaded shaft, a chamber in the shaft to engage a second screw and a pointed tip.

FIG. 3 illustrates various exemplary embodiments in which the shaft 310 of the screw comprising a chamber 700 for receiving a second screw, is threaded 330 from the tip 320 to the head 300. The chamber 700 of the screw can have threading 710 that can be the same thread pitch or a different thread pitch of the threading of the shaft of the screw comprising the chamber 700.

Figure 5:
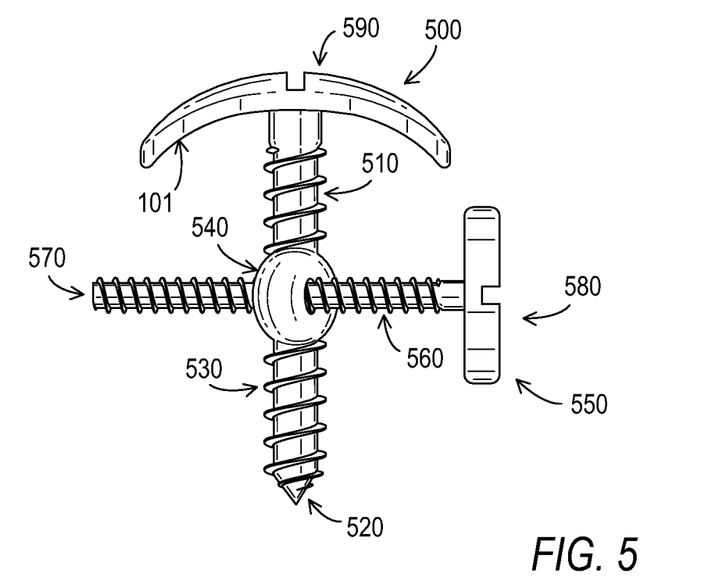
FIG. 5: illustrates an embodiment of an implantable device including a second screw engaged in the chamber of the first screw at a perpendicular angle.

FIG. 5 illustrates various embodiments in which a first screw 590, comprises a head 500, a shaft 510, a tip 520 and a chamber 540 located on the shaft 510 of the screw 590. In some embodiments the head 500 is contoured, the shaft 510 is threaded 530, and the tip 520 is adapted to penetrate bone tissue. Further, in some embodiments, the chamber 540 is oriented on the shaft 510 of the first screw 590, such that a second screw 580, having a head 550, a shaft 560, and a tip 570, can be inserted into the chamber 540 at an angle perpendicular to that of the first screw 590.

FIG. 6 illustrates various embodiments in which a first screw 690 comprises a head 600, a shaft 610, a tip 620 and a chamber 640 located on the shaft 610 of the screw 690. In some embodiments the head 600 is contoured, the shaft 610 is threaded 630, and the tip 620 is adapted to penetrate bone tissue. Further, in some embodiments, the chamber 640 is oriented on the shaft 610 of the first screw 690, such that a second screw 680, having a head 650, a shaft 660, and a tip 670, traverses the first screw 690 at an angle that is either oblique or acute to the first screw 690.

As illustrated in FIG. 6, various exemplary embodiments provide that the shaft 610 of the receiving screw 690, comprising a threaded chamber 640, is larger than the diameter of the shaft 660 of the second screw 680 that is inserted into the threaded chamber 640.

Figure 4:
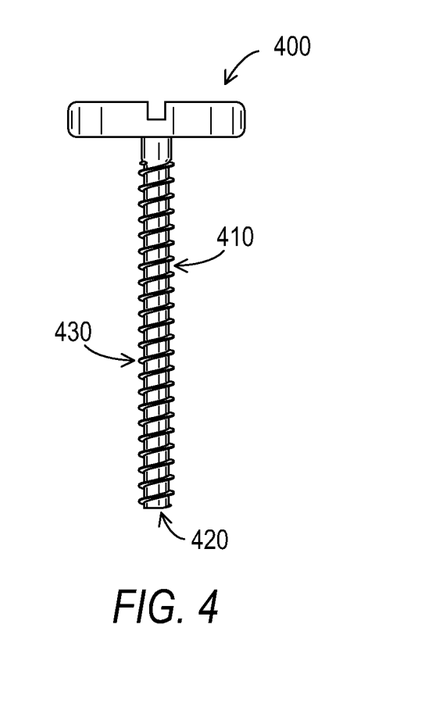
FIG. 4: illustrates an embodiment of an implantable device including a head, a shaft and a tip.

FIG. 4 illustrates some exemplary embodiments in which the head of a screw 400 is not contoured (e.g., flat, square, rectangular shaped, or the like) and the tip 420 of the screw not adapted to penetrate bone tissue. While not intended to be limiting, a screw as illustrated in FIG. 4 may be used as a mating screw for insertion into the chamber of another screw. In various embodiments, this type of screw may be inserted or turned into the chamber of the first screw.

Further, by way of some exemplary embodiments, the chamber for receiving a second screw can include an internal structure such that threading is not required to securely engage a second screw. Similarly, in various other exemplary embodiments, the screw to be inserted into the chamber can have a shaft structure such that threading is not required to securely engage the chamber of a screw. Thus, in some embodiments, the first screw receives through a chamber in the shaft, a second screw by some securing means other than by complementary threading. For example, the diameter of the chamber may be slightly smaller than the diameter of the shaft of the second screw and the user pushes the second screw through the chamber. In some embodiments, the chamber may comprises compressible and expandable shape memory alloys that surround the opening of the chamber and hold the second screw in place after it is inserted in the chamber. In some embodiments, the chamber comprises a channel, groove, or slit that with a geometry that is adapted to receive at least a portion of the shaft and/or tip of the first screw.

In various exemplary embodiments, the length of each screw may range from about 4 mm to about 20 mm. In some embodiments, each of the screws described herein may have a diameter ranging from about 1.2 mm to about 3 mm. The specific dimensions of each screw may be determined by the requirements of the procedure being performed.

In various embodiments, the head of the screw may have one or more recessed and/or projections that may be any size and shape (e.g., straight, flat-sided shape, an elliptical shape, bi-concave shape, square shape, or any other protruding or recessed shape which provides sufficient implantation tool-engaging end strength and drive purchase to allow transmission of insertional torque without breaking or otherwise damaging the implantable screw.

The implantation tool includes, but is not limited to, driver, wrench, spanner, screwdriver, or other turning tool, and the like that can engage the implantable device. The implantation tool may be used manually (e.g., turnable by hand) or by an automatic device (e.g., using a drill, power driver, etc.).

Sterilization

The implant may be sterilizable. In various embodiments, one or more components of the device are sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

Kits

In various embodiments, an implantable device may be packaged in a kit in order to maintain the device in a sterile environment before it is implanted. In various embodiments, a kit is provided comprising one or more implantable screws. The kit may include additional parts along with the implantable screw combined together to be used to implant the screw. The kit may include the implantable screw(s) in a first compartment. The second compartment may include instruments needed for implanting the screw (such as for example, implantation tool, driver, etc.). A third compartment may include gloves, drapes, wound dressings and other procedural supplies for maintaining sterility of the implanting process, as well as an instruction booklet. A fourth compartment may include additional needles and/or sutures. In a fifth compartment, the kit may include osteoinductive and/or osteoconductive agents (e.g., BMP) for application into the space created by the contoured head. Each tool may be separately packaged in a plastic pouch that is radiation sterilized. A cover of the kit may include illustrations of the implanting procedure and a clear plastic cover may be placed over the compartments to maintain sterility.

In some embodiments, the jawbone is prepared using conventional surgical procedures and the device can be inserted in accordance with the conventional means.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed:

1. An implantable screw for maintaining space during bone grafting in dental regenerative procedures in a jaw of a patient in need of such treatment, the implantable screw comprising:
    a contoured head having a region adapted to support soft tissue of the jaw and a region to permit bone growth, the contoured head having a maximum width between a planar first end surface and a planar second end surface, said contoured head having a concave under surface and a convex upper surface opposite the under surface; and
    a threaded shaft defining a long axis and extending from the under surface, the shaft including a tip adapted to penetrate bone tissue and a chamber defining a throughhole that extends transverse to the long axis through the shaft, wherein the screw is bioresorbable and comprises cortical bone material.

2. An implantable screw of claim 1, wherein the contoured head ranges in size from about 3 mm to about 10 mm.

3. An implantable screw of claim 1, wherein the threading pitch allows for stability after engagement of about 3 mm to about 4 mm of bone.

4. An implantable screw of claim 1, wherein the shaft of the screw is partially threaded above the tip to a point on the shaft less than the entire length of the shaft.

5. An implantable screw of claim 4, wherein the chamber is configured for horizontally engaging a second screw, wherein the second screw comprises a head, a shaft and a tip.

6. An implantable screw of claim 5, wherein the chamber is threaded to receive the second threaded screw.

7. An implantable screw of claim 5, wherein the chamber is adapted to receive the second screw at a perpendicular angle to the screw so as to allow both horizontal and vertical bone growth.

8. An implantable screw of claim 5, wherein the shaft of the first screw has a diameter larger than the shaft of the second screw.

9. An implantable screw of claim 1, wherein the length of the screw from head to tip is about 4 mm to about 20 mm.

10. An implantable screw of claim 1, wherein the diameter of the screw is from about 1.2 mm to about 3 mm.

11. An implantable screw of claim 1, wherein the throughhole is threaded.

12. An implantable screw of claim 1, wherein the shaft comprises a first thread form between the chamber and the head and a second thread form between the chamber and the tip.

13. An implantable device for maintaining space during bone grafting in dental regeneration procedures in a jaw of a patient in need of such treatment, the implantable device comprising:
    a first screw comprising:
        a contoured head having a region adapted to receive soft tissue of the jaw, the head having a maximum width between a planar first end surface and a planar second end surface, said contoured head having a concave under surface and a convex upper surface opposite the under surface,
        a threaded shaft extending from the under surface of the head along a longitudinal axis for holding the screw in bone, the shaft including a tip having a solid configuration adapted to penetrate bone tissue, and
        a chamber disposed below the contoured head and above the tip of the first screw; and
    a second screw comprising:
        a head, and
        a shaft including a tip, wherein at least a portion of the shaft and the tip of the second screw are adapted to be received by the chamber of the first screw;
    wherein the first screw is bioresorbable and comprises cortical bone material, an outer surface of the first screw is at least partially demineralized, and the first and second end surfaces extend parallel to the longitudinal axis.

14. An implantable device of claim 13, wherein the second screw comprises cortical bone material and the chamber of the first screw is threaded to receive the second screw, and the shaft of the second screw is threaded.

15. An implantable device of claim 13, wherein the length of the first screw is from about 4 mm to about 20 mm.

16. An implantable device of claim 13, wherein the chamber is positioned to receive the second screw at a perpendicular angle to the first screw so as to allow horizontal and vertical bone growth.

17. An implantable device of claim 13, wherein the diameter of the first screw is from about 1.2 mm to about 3 mm.

18. An implantable device of claim 13, wherein the shaft of the first screw has a diameter larger than the shaft of the second screw.

19. An implantable device of claim 13, wherein the second screw comprises cortical bone material.

20. An implantable screw for maintaining space during bone grafting in dental regenerative procedures in a jaw of a patient in need of such treatment, the implantable screw comprising:
    a contoured head having a region adapted to support soft tissue of the jaw and a region to permit bone growth, the contoured head having a maximum width between a planar first end surface and a planar second end surface, said contoured head having a concave under surface and a convex upper surface opposite the under surface;

a threaded shaft defining a long axis and extending from the under surface of the head and including a tip adapted to penetrate bone tissue, the shaft comprising a chamber defining a throughhole that extends through the shaft along a horizontal axis that is perpendicular to the long axis, wherein the screw is bioresorbable and wherein the screw comprises cortical bone material.

* * * * *